(12) United States Patent
Ohkouchi

(10) Patent No.: US 10,939,060 B2
(45) Date of Patent: Mar. 2, 2021

(54) IMAGE SENSOR, MEASURING DEVICE, AND MEASURING METHOD

(71) Applicant: NIKON CORPORATION, Tokyo (JP)

(72) Inventor: Naoki Ohkouchi, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 77 days.

(21) Appl. No.: 15/981,466

(22) Filed: May 16, 2018

(65) Prior Publication Data

US 2018/0262702 A1 Sep. 13, 2018

Related U.S. Application Data

(63) Continuation of application No. PCT/JP2016/084277, filed on Nov. 18, 2016.

(30) Foreign Application Priority Data

Nov. 18, 2015 (JP) .............................. JP2015-225948

(51) Int. Cl.
*G06T 11/00* (2006.01)
*H04N 5/217* (2011.01)
(Continued)

(52) U.S. Cl.
CPC ......... *H04N 5/3575* (2013.01); *A61B 5/0066* (2013.01); *G01N 21/17* (2013.01);
(Continued)

(58) Field of Classification Search
None
See application file for complete search history.

(56) References Cited

U.S. PATENT DOCUMENTS

| | | | |
|---|---|---|---|
| 6,020,963 A | 2/2000 | DiMarzio | |
| 2006/0077395 A1* | 4/2006 | Chan | G01B 11/2441 |
| | | | 356/497 |
| 2011/0187908 A1* | 8/2011 | Kawahito | H01L 27/14603 |
| | | | 348/306 |
| 2014/0055749 A1 | 2/2014 | Zhou et al. | |
| 2014/0126694 A1* | 5/2014 | Abenaim | G01V 5/0008 |
| | | | 378/57 |

(Continued)

FOREIGN PATENT DOCUMENTS

| | | |
|---|---|---|
| JP | 10-241611 | 9/1998 |
| JP | 2009-270879 | 11/2009 |

(Continued)

OTHER PUBLICATIONS

Kadambi A, Taannazyan V, Jayasuriya S, Raskar R. Frequency domain TOF: encoding object depth in modulation frequency. arXiv preprint arXiv:1503.01804. Mar. 5, 2015. (Year: 2015).*

(Continued)

*Primary Examiner* — Clifford Hilaire

(57) ABSTRACT

An image sensor that captures an image of light from a predetermined depth of a subject, includes: a photoelectric converter that photoelectrically converts light including interference light of light from the subject and reference light; a discrimination unit that locks in and detects a signal component having an interference frequency in an interference light component corresponding to the predetermined depth from a signal output from the photoelectric converter; and a floating diffusion unit that temporarily accumulates an electric charge resulting from the photoelectric conversion by the photoelectric converter; wherein: the discrimination unit includes: a transfer unit that transfers the signal to the floating diffusion unit; and a sampling unit that samples the electric charge accumulated in the floating diffusion unit at a sampling frequency determined based on the interference frequency.

15 Claims, 9 Drawing Sheets

(51) Int. Cl.
*H04N 5/357* (2011.01)
*G01N 21/17* (2006.01)
*A61B 5/00* (2006.01)
*H04N 13/296* (2018.01)
*H04N 13/00* (2018.01)

(52) U.S. Cl.
CPC ......... *G06T 11/005* (2013.01); *H04N 5/2173* (2013.01); *H04N 13/296* (2018.05); *G06T 2207/10101* (2013.01); *H04N 2013/0081* (2013.01)

(56) References Cited

U.S. PATENT DOCUMENTS

| | | | | |
|---|---|---|---|---|
| 2014/0147928 | A1* | 5/2014 | Steinebach | G01N 21/59 436/164 |
| 2015/0077590 | A1 | 3/2015 | Kuriyama et al. | |
| 2016/0165159 | A1* | 6/2016 | Hseih | H04N 5/23235 348/273 |

FOREIGN PATENT DOCUMENTS

| | | |
|---|---|---|
| JP | 2011-196771 | 10/2011 |
| JP | 2014-115161 | 6/2014 |
| WO | WO 2013/164915 A1 | 11/2013 |
| WO | WO 2015/001918 A1 | 1/2015 |

OTHER PUBLICATIONS

English Translation by WIPO of the International Preliminary Report on Patentability dated Jul. 2, 2017, in corresponding International Patent Application No. PCT/JP2016/084277, 6 pgs.
Abe Takashi et al. "CMOS Image Sensors Comprised of Floating Diffusion Driving Pixels With Buried Photodiode" IEEE Journal of Solid-State Circuits, vol. 39, No. 12, Dec. 12, 2004, XP011122678, pp. 2408-2416.
Extended European Search Report dated May 20, 2019 in corresponding European Patent Application No. 16866442.3 (10 pages).
Japanese Office Action dated May 21, 2019 in corresponding Japanese Patent Application No. 2017-551948 (4 pages).
English Translation by WIPO of the International Preliminary Report on Patentability dated Feb. 7, 2017, in corresponding International Patent Application No. PCT/JP2016/084277, 6 pgs.
Office Communication dated May 14, 2020, in European Patent Application No. 16866442.3.
European Office Action dated Dec. 17, 2019 in corresponding European Patent Application No. 16866442.3.
International Search Report dated Feb. 7, 2017 in corresponding International Patent Application No. PCT/JP2016/084277.
Written Opinion of the International Search Authority dated Feb. 7, 2017 in corresponding International Patent Application No. PCT/JP2016/084277.

\* cited by examiner

IMAGE SENSOR, MEASURING DEVICE, AND MEASURING METHOD

This application is a continuation of International Application No. PCT/JP2016/084277 filed Nov. 18, 2016.

INCORPORATION BY REFERENCE

The disclosures of the following priority application and the International Application are herein incorporated by reference:
Japanese Patent Application No. 2015-225948 filed Nov. 18, 2015; and
International Application No. PCT/JP2016/084277 filed Nov. 18, 2016.

BACKGROUND OF THE INVENTION

1. Field of the Invention

The present invention relates to an image sensor, a measuring device, and a measuring method.

2. Description of Related Art

A technology of measuring images from the inside of a subject using light interference, which is called OCT (Optical Coherence Tomography), is known. In the OCT, for example, a subject is irradiated with coherent light using a wavelength variable light source, and a pixel signal obtained by image-capturing is subjected to frequency separation to extract a signal component from a predetermined depth.

In an optical tomographic image generating device in Japanese Laid-Open Patent Publication No. 2009-270879, pixel signals are subjected to frequency separation by Fourier transform. With this method, however, leakage errors occur if a phase of a signal start point is different from a phase of a signal end point of the pixel signal obtained by one sweep of an oscillation frequency of measurement light changed with time. This fails to accurately extract a frequency component to be separated. Thus, a method for performing more accurate frequency separation is required.

SUMMARY OF INVENTION

According to the 1st aspect of the present invention, an image sensor that captures an image of light from a predetermined depth of a subject, comprises: a photoelectric converter that photoelectrically converts light comprising interference light of light from the subject and reference light; a discrimination unit that locks in and detects a signal component having an interference frequency in an interference light component corresponding to the predetermined depth from a signal output from the photoelectric converter; and a floating diffusion unit that temporarily accumulates an electric charge resulting from the photoelectric conversion by the photoelectric converter; wherein: the discrimination unit comprises: a transfer unit that transfers the signal to the floating diffusion unit; and a sampling unit that samples the electric charge accumulated in the floating diffusion unit at a sampling frequency determined based on the interference frequency.

According to the 2nd aspect of the present invention, in the image sensor according to the 1st aspect, it is preferred that the image sensor comprises a plurality of pixels; the photoelectric converter is arranged in each of the plurality of pixels; and the discrimination unit is arranged for each pixel or for each block comprising two or more pixels, and locks in and detects a signal component having the interference frequency from the signal output from the photoelectric converter of the corresponding pixel or block.

According to the 3rd aspect of the present invention, in the image sensor according to the 1st aspect, it is preferred that the discrimination unit is partly or entirely arranged in a layer different from a layer in which the photoelectric converter is arranged.

According to the 4th aspect of the present invention, in the image sensor according to the 2nd aspect, it is preferred that the discrimination unit is partly or entirely arranged in a layer different from a layer in which the photoelectric converter is arranged.

According to the 5th aspect of the present invention, in the image sensor according to the 1st aspect, it is preferred that the discrimination unit comprises: a multiplication unit that multiplies a signal output from the sampling unit by a reference signal having the interference frequency; and a first filtering unit that separates a component having a low frequency equal to or less than a predetermined value and a direct current component from a signal output from the multiplication unit.

According to the 6th aspect of the present invention, in the image sensor according to the 1st aspect, it is preferred that the transfer unit transfers the signal to the floating diffusion when the transfer unit is in its on state while switching between the on state and an off state at a switching frequency based on the interference frequency; and the discrimination unit comprises a second filtering unit that separates a component having a low frequency equal to or less than a predetermined value and a direct current component from a signal output from the sampling unit.

According to the 7th aspect of the present invention, in the image sensor according to the 1st aspect, it is preferred that the image sensor captures an image of interference light of light comprising light from a first depth and light from a second depth, the second depth being larger than the first depth, and the reference light; and the sampling unit performs a larger number of samplings corresponding to the second depth than a number of samplings corresponding to the first depth.

According to the 8th aspect of the present invention, in the image sensor according to the 2nd aspect, it is preferred that the image sensor captures an image of interference light of light waves from a plurality of depths and the reference light; and the discrimination unit locks in and detects signal components having a plurality of the interference frequencies in a plurality of the interference light components corresponding to the plurality of depths from the signal output from the photoelectric converter, for each of the pixels or the blocks.

According to the 9th aspect of the present invention, in the image sensor according to the 8th aspect, it is preferred that the discrimination unit locks in and detects signal components having the plurality of interference frequencies in the plurality of interference light components corresponding to the plurality of depths from the signal output from the photoelectric converter, for each of the blocks; and the interference frequencies for the plurality of pixels included in one of the blocks are different from each other.

According to the 10th aspect of the present invention, a measuring device comprises: the image sensor according to 1st aspect; a wavelength variable light generator that generates wavelength variable light having a wavelength changed with time; and a separator that separates the reference light and measurement light that is coherent with the reference light from the wavelength variable light generated by the wavelength variable light generator, and irradiates the subject with the measurement light.

According to the 11th aspect of the present invention, in the measuring device according to the 10th aspect, it is preferred that the wavelength variable light generator generates wavelength variable light having a wavelength varying with time in a near-infrared range.

According to the 12th aspect of the present invention, in the measuring device according to the 10th aspect, the device further comprises: a polarization splitter that splits the reference light into light having a first polarized light component and light having a second polarized light component, the second polarized light component being perpendicular to the first polarized light component, wherein: the photoelectric converter comprises a first photoelectric converter that photoelectrically converts reference light of the first polarization component, and a second photoelectric converter that photoelectrically converts light comprising interference light of the reference light having the second polarization component and reflected light from the predetermined depth of the subject irradiated with the measurement light; and the discrimination unit comprises a noise reduction unit that reduces noises of a signal output from the second photoelectric converter based on a signal output from the first photoelectric converter, wherein a signal component having the interference frequency is locked-in and detected from the signal output from the second photoelectric converter.

According to the 13th aspect of the present invention, a measuring method of measuring light from a predetermined depth of a subject by a measurement system comprising a light generator that generates coherent light, a separator that separates the light, a photoelectric converter, a floating diffusion unit that temporarily accumulates an electric charge resulting from the photoelectric conversion by the photoelectric converter, and a processor that processes a signal from the photoelectric converter, comprises: generating wavelength variable light having a wavelength changed with time, by the light generator; separating reference light and measurement light that is coherent with the reference light from the wavelength variable light and irradiating the subject with the measurement light, by the separator; photoelectrically converting light comprising interference light of the reference light and reflected light from the predetermined depth of the subject irradiated with the measurement light, by the photoelectric converter; and locking in and detecting a signal component having an interference frequency in an interference light component corresponding to the predetermined depth from a signal output from the photoelectric converter, by the processor, wherein: the signal is transferred to the floating diffusion unit by the processor and the electric charge accumulated in the floating diffusion unit is sampled at a sampling frequency determined based on the interference frequency by the processor.

BRIEF DESCRIPTION OF DRAWINGS

FIG. 3 is a diagram illustrating a method of extracting intensity of a specific frequency component by lock-in.

DESCRIPTION OF EMBODIMENTS

A measuring device according to one embodiment will be described hereinafter with reference to the drawings as appropriate. The measuring device according to the present embodiment acquires information on light from a predetermined depth of a subject, using light interference. Particularly, the measuring device constructs tomographic images of the inside of the subject.

Figure 1:
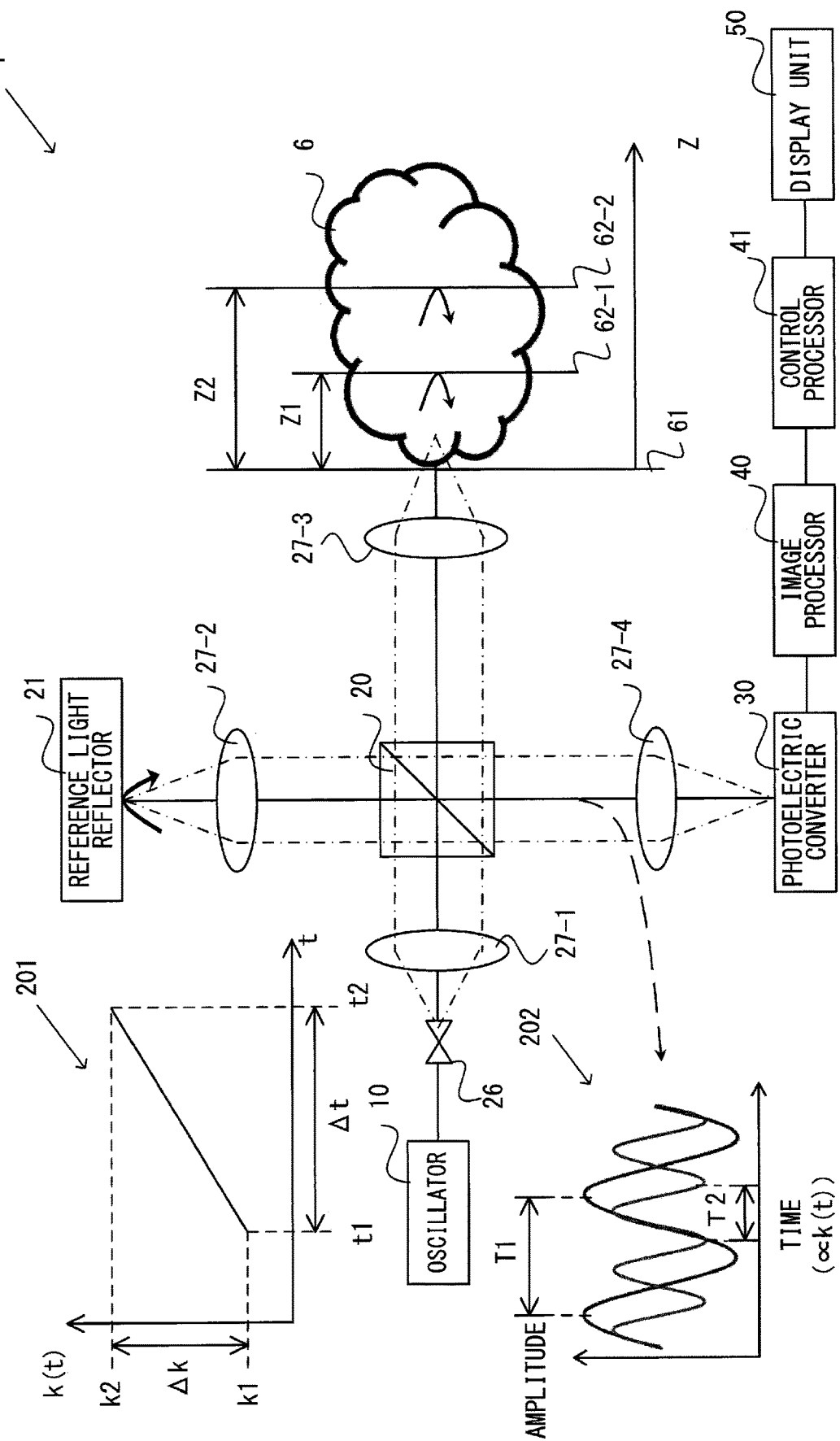
FIG. 1 is a schematic diagram of a measurement device according to one embodiment.

FIG. 1 is a schematic diagram illustrating a configuration of the measuring device 1 according to the present embodiment. The measuring device 1 is an interferometric measuring device using SS-OCT (Swept Source-OCT) in which a wavelength of oscillating light is changed with time to separate light from a predetermined depth based on a period of interference occurrence. The measuring device 1 comprises an oscillator 10, a separator 20, a reference light reflector 21, a photoelectric converter 30, an image processor 40, a control processor 41, a display unit 50, a spatial filter (hereinafter referred to as SF) 26, and lenses 27-1, 27-2, 27-3, 27-4. In the present embodiment, an image sensor (a stacked image sensor 100 described later), which performs photoelectric conversion, also preferably performs processing such as frequency separation of pixel signals in the image processor 40.

It should be noted that the processing such as frequency separation of signals resulting from the photoelectric conversion by the photoelectric converter 30 may be performed by a processing device arranged outside an image sensor. Although a subject 6 is planarly irradiated with measurement light in an image-forming optical system in the present embodiment, the SF 26 and the lenses 27-1, 27-2, 27-3, 27-4 may be omitted in the case of point sensors or other sensors.

The oscillator 10 comprises an oscillating device that oscillates coherent light while varying a wavelength of the light with time, such as a frequency domain mode locked laser. The oscillator 10 serves as a wavelength variable light generator. Preferably, light emitted from the oscillator 10 has a wavelength range from visible light to millimeter wave. With light in this wavelength range, light reflected from the inside of the subject 6 can be obtained by taking advantage of characteristics such as permeability of light at each wavelength. Further preferably, the oscillating light from the oscillator 10 is near-infrared light having a wavelength of 800 nm to 1300 nm. This enables an image of a deep part of a subject to be obtained with near-infrared light having a high bio-permeability while avoiding light absorption by water.

The oscillator 10 changes the wavelength of oscillating light in such a manner that the wave number of the light increases at a constant rate as a function of measurement time so that an interference period becomes constant. For the sake of simplification of description, the following description thus refers to the wave number, which is defined as the reciprocal of wavelength, instead of wavelength. FIG. 1 illustrates a wave number-time characteristic graph 201 of light from the oscillator 10. In the wave number-time characteristic graph 201, wave number k(t) has a linear relationship with time t. The oscillator 10 sweeps the wave number to increase the value thereof by Δk from k1 to k2 during a time Δt from t1 to t2. By repeating this sweep as appropriate, information on a plurality of depths of interest can be obtained.

It should be noted that the relationship between the wave number and the measurement time can be set as desired, as long as the pixel signal is processed as appropriate so that the frequency separation can be performed on a quantitative basis.

The light emitted from the oscillator 10 is changed by the SF 26 into divergent light, which is then converged by the lens 27-1 to be incident on the separator 20.

It should be noted that the light emitted from the oscillator 10 may be diverged by a diverging lens, instead of the SF 26.

The separator 20 comprises an optical element such as a beam splitter to separate light emitted from the lens 27-1 into reference light and measurement light and then emit the reference light toward the reference light reflector 21 and emit the measurement light toward the subject 6. The emitted reference light is converged by the objective lens 27-2, and the reference light reflector 21 is planarly irradiated with the reference light. The emitted measurement light is converged by the objective lens 27-3 comparable to the objective lens for the reference light, and the subject 6 is planarly irradiated with the measurement light.

The reference light reflector 21 comprises an optical mirror or other elements to reflect the reference light, which has been emitted from the separator 20 and is incident on the reference light reflector 21 through the objective lens 27-2, and emit back the light through the objective lens 27-2 to the separator 20. Each bent solid arrow in FIG. 1 indicates that the light is reflected from each surface.

Although the present embodiment uses a Michelson interference system which is a reflecting optical system, a Mach-Zehnder interference system which is a transmitting optical system may be used without providing the reference light reflector 21. This can reduce or eliminate ghosts due to multiple reflections.

The measuring device 1 according to the present embodiment captures images of measurement light reflected from planes at a plurality of depths of the subject 6, with a surface of the subject 6 as a reference plane 61. For example, FIG. 1 illustrates a measurement plane 62-1 at a depth Z1 and a measurement plane 62-2 at a depth Z2 from the reference plane 61 of the subject 6.

Instead of analyzing information from depths of the subject 6 on a planar basis, the measuring device 1 may be used as a point sensor to analyze information on the depth of each point along an optical axis of measurement light inside the subject 6. Additionally, the reference plane is not limited to the surface of the subject 6 and may be set as desired.

The light reflected from the inside of the subject 6 is incident on the separator 20 through the objective lens 27-3. The separator 20 combines the measurement light reflected from the inside of the subject 6 and the reference light, which is incident from the reference light reflector 21, in a coherent manner and emits the combined light to the photoelectric converter 30 through the condenser lens 27-4. The condenser lens 27-4 is a lens for forming an image of interference light of the reference light and the measurement light to the subject 6 on an area sensor of the photoelectric converter 30, wherein the area sensor is planarly irradiated with interference light of light waves reflected from the same depth of the subject 6. A graph 202, which is illustrated at a position indicated by a dashed arrow, schematically represents each amplitude of the interference light of the light from each of the depths Z1 and Z2 of the subject 6 and the reference light, as a function of measurement time. As is apparent with reference to the graph 202, the light waves from the different depths Z1 and Z2 of the subject 6 are measured as interference light having different interference periods. Generally, light reflected from a deeper position has a smaller amplitude.

The photoelectric converter 30 comprises a photoelectric conversion element such as a photodiode (hereinafter referred to as PD) and photoelectrically converts the interference light of the reference light and light that is reflected light of measurement light and is reflected from the subject 6, which are incident from the separator 20, to output a signal to the image processor 40. The photoelectric converter 30 according to the present embodiment comprises a PD of the image sensor 100. As will be described later, the image sensor 100 comprises a PD for each pixel, and a signal resulting from photoelectric conversion by the PD is output to a processing circuit arranged for each pixel. For the measuring device 1 as a point sensor, a single PD constitutes the photoelectric converter 30. For the measuring device 1 as a point sensor, a high SN may be achieved by removing common noises and in-phase components of the measurement system by a balance detector.

The image processor 40 comprises a processing circuit of the image sensor 100 and performs frequency separation processing on an output signal from the photoelectric converter 30 to extract a signal component from a predetermined depth. The image processor 40 serves as a discrimination unit under the control of the control processor 41. The frequency separation of the output signal is achieved by processing on the output signal equivalent to multiplication of the output signal by a reference signal having a frequency corresponding to a predetermined depth.

It should be noted that the processing circuit for processing the signal resulting from the photoelectric conversion and the image processor 40 may be arranged not for each pixel, but for each pixel block including a plurality of pixels. The image processor 40 may be arranged outside the image sensor 100.

When the wave number oscillated by the oscillator 10 changes by dk, a phase difference between the light that is reflected light of the measurement light and is reflected from a depth Z of the subject 6 and the reference light changes by $d\theta = dk \times 2 \times Z$. The interference light of the reference light and the light that is reflected light of the measurement light and is reflected from the subject 6 oscillates and repeats light and dark a number of times that is equal to the number of times of a phase dθ reaching integer times of $2\pi$. In other words, the interference light repeats a cycle of light and dark, every time dk increases by $\pi/Z$. If the oscillator 10 sweeps the wave number while maintaining a linear relationship between the wave number and the time as in the present embodiment, the interference period is constant for a given depth Z and the interference period is inversely proportional to the depth. The reciprocal of the interference period is hereinafter referred to as an interference frequency. At the time of the frequency separation of the signal resulting from the photoelectric conversion of the interference light, the interference frequency serves as the frequency of the reference signal for lock-in.

Although the above description assumes that the refractive index of the inside of the subject 6 is 1, it is desirable to calculate the values based on an effective optical path length as appropriate depending on the refractive index of the inside of the subject 6. For example, if the refractive index of the inside of the subject 6 is uniformly n, Z in the above calculation formula should be replaced by nZ for calculation.

Figure 2:
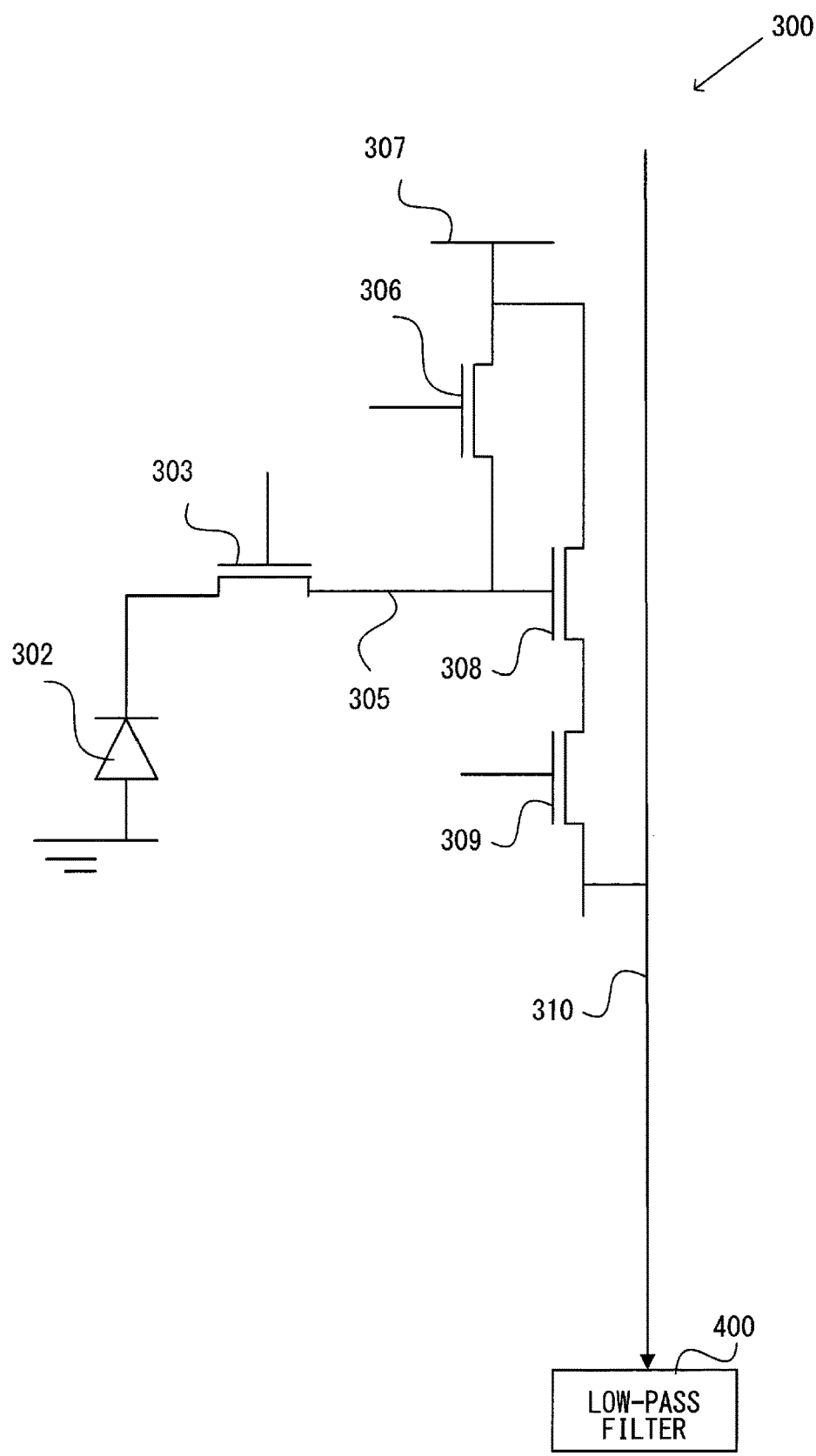
FIG. 2 is a schematic diagram illustrating a configuration of a processing circuit in a stacked image sensor according to one embodiment.

FIG. 2 is a diagram illustrating a configuration of a current-voltage conversion circuit 300 of the image sensor 100 for performing a current-voltage conversion on the electric current signal resulting from the photoelectric conversion to output the resulting signal. The current-voltage conversion circuit 300 is a part of the processing circuit of the image processor 40 which serves as a discrimination unit. The current-voltage conversion circuit 300 comprises a PD 302, a transfer gate 303, a floating diffusion (hereinafter referred to as FD) 305, a reset transistor 306, a VDD 307, an amplification transistor 308, a row selection transistor 309, and a vertical signal line 310.

The PD 302 photoelectrically converts interference light of the reference light and the light that is reflected light of the measurement light and is reflected from the subject 6. An electric charge resulting from the photoelectric conversion is transferred to the FD 305 by the transfer gate 303 which serves as a transfer unit. Based on a control from a transfer signal line (not illustrated in the figure), the transfer gate 303 switches between its on state and off state at a frequency twice as high as the interference frequency, and transfers the electric charge resulting from the photoelectric conversion to the FD 305 at a timing based on a predetermined sampling frequency when the transfer gate 303 is in its on state. This allows the transfer gate 303 to output a signal equivalent to a signal sampled at the sampling frequency multiplied by a rectangular wave signal having the interference frequency. In other words, the transfer gate 303 also serves as a sampling unit and a multiplication unit.

Figure 3:
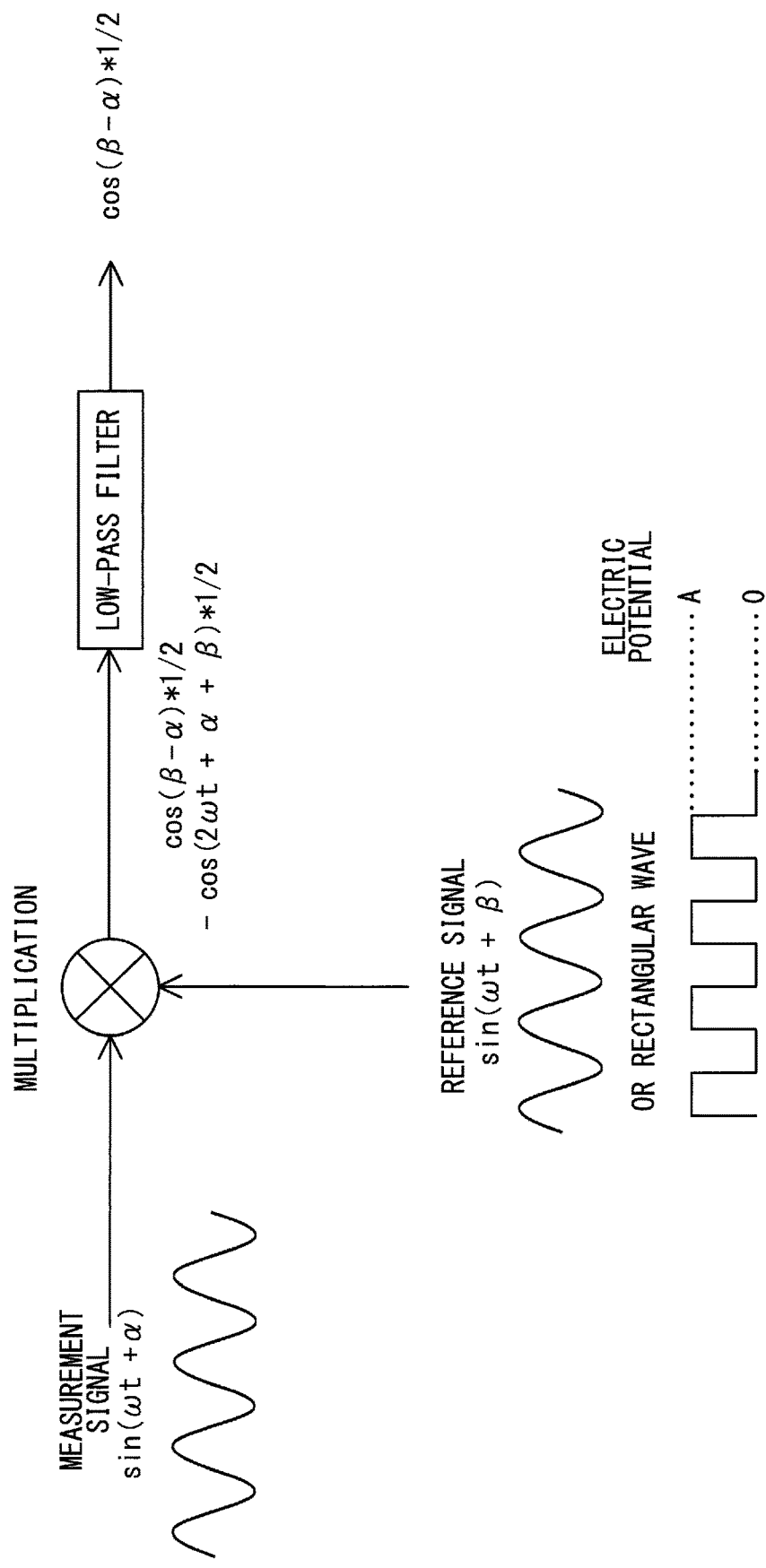

FIG. 3 is a conceptual diagram of frequency separation by lock-in. In order to extract a component having a frequency ω from a measurement signal by the lock-in, the measurement signal is multiplied by a sine wave having the same frequency ω as a reference signal to separate the signal into a direct current component and a component having a frequency 2ω. The direct current component is then extracted by the low-pass filter. Here, approximately, the reference signal may be a rectangular wave having the frequency ω. The on state of the transfer gate 303 described above corresponds to a state in which an output voltage of the rectangular wave has a value of A, while the off state corresponds to a state in which the output voltage of the rectangular wave has a value of 0.

The electric charge transferred to the FD 305 is output by the amplification transistor 308 as a voltage signal, which is read out from the vertical signal line 310 at the sampling frequency under the control of the row selection transistor 309. A direct current component and/or a low frequency component are extracted from the output voltage signal by a low-pass filter 400 and, based on these values, the signal intensity of a signal component corresponding to a predetermined depth of the subject 6 is calculated. Preferably, the signal intensity is the amplitude of the value of the direct current component. When a potential of the FD 305 is read out, the potential in the FD 305 is reset by the reset transistor 306 and the VDD 307.

Figure 4:
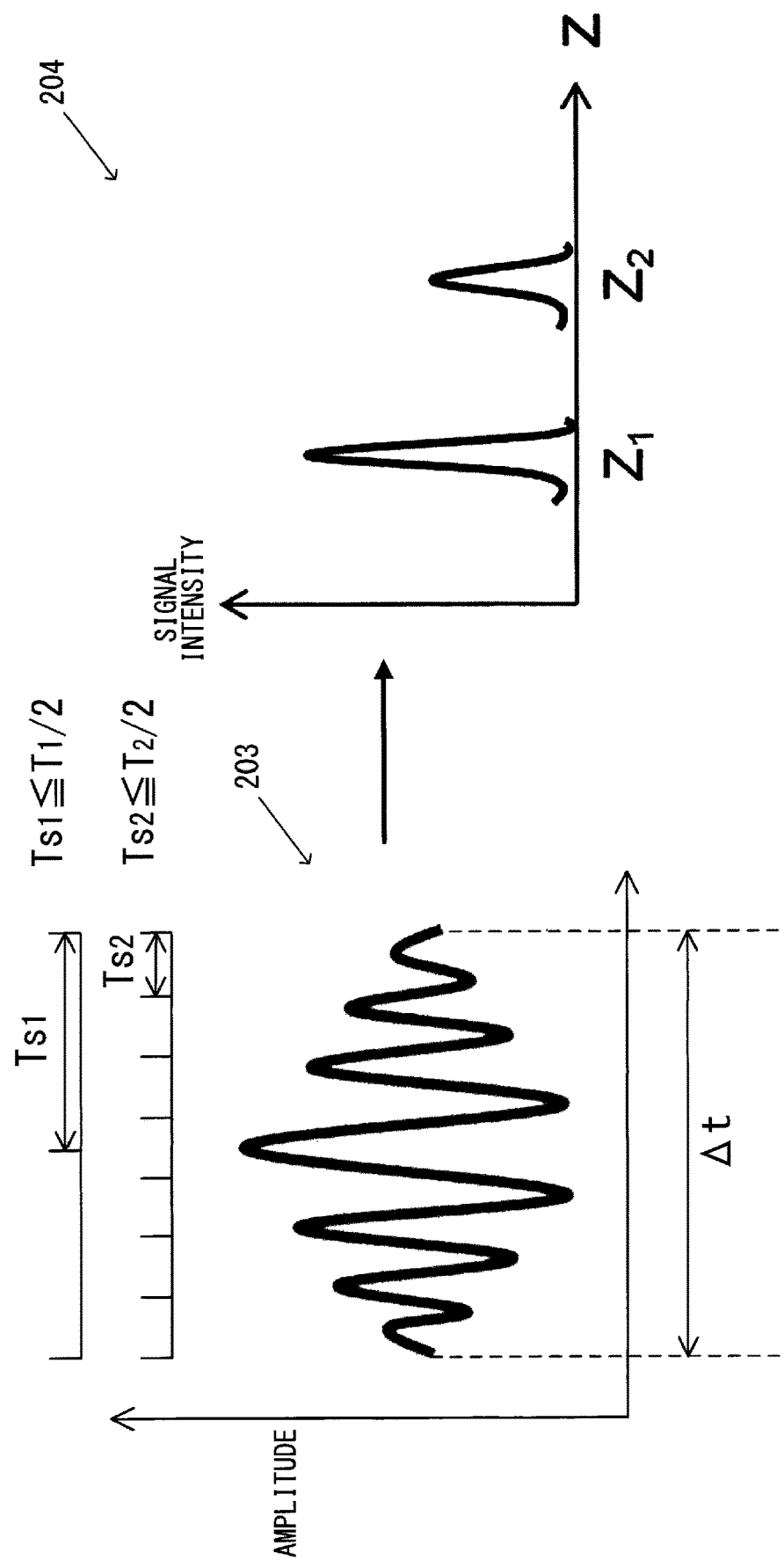
FIG. 4 is a conceptual diagram illustrating a method of frequency separation in one embodiment.

FIG. 4 is a view illustrating a method of determining the sampling frequency. A sampling period Ts1 (the reciprocal of the sampling frequency) for extracting a signal from a depth Z1 of the subject 6 is set to a value equal to or less than a half of the interference period T1 corresponding to the depth Z1 according to the sampling theorem. Similarly, a sampling period Ts2 for extracting a signal from a depth Z2 of the subject 6 is set to a value equal to or less than a half of the interference period T2 corresponding to the depth Z2 according to the sampling theorem. The amplitude of the interference light from the depths Z1 and Z2 forms a waveform in which a wave having a longer period T1 is superposed by a wave having a shorter period T2, as illustrated in a graph 203. The interference light is subjected to photoelectric conversion and frequency separation to remove other signals, so that the intensities of signal components from the depths Z1 and Z2 of the subject 6 corresponding to the individual interference frequencies can be quantitatively calculated. A graph 204 illustrates a schematic diagram of a power spectrum in which the horizontal axis represents the depth Z of the subject 6 corresponding to the interference frequency and the vertical axis represents the signal intensity.

Using the lock-in as means for frequency discrimination as in the present embodiment, instead of Fast Fourier transform (hereinafter referred to as FFT), makes it possible to detect weak interference light of light reflected back from a deep part in a living body, which is weak due to the light having partly scattered and attenuated, and reference light, with a high sensitivity.

Furthermore, in order to mount an SS-OCT including a point sensor (corresponding to one pixel) and FFT as the following processing means on a two-dimensional image sensor, the FFT has to be linked to each pixel. Since it is necessary to accumulate sampling data for applying the FFT to each pixel and calculate a power spectrum from the data by the FFT, more memory for the sampling data accumulation is required in proportion to an increase in the number of pixels. This leads to an increase in required memory capacity. By contrast, in the measuring device 1 according to the present embodiment, an output value of an amplitude sampled at the frequency of the reference signal in the lock-in corresponds to an output value at a deep part of the subject 6 corresponding to the frequency in a pixel part. This eliminates the need for large sampling data required for the FFT processing. Thus, although large sampling data described above is required for power spectrum analysis by the FFT in order to acquire a cross-sectional image at a fixed depth of the subject 6, for example, it is possible in the lock-in scheme of the present embodiment to form an image collectively from output values of pixels sampled by the reference signal at the frequency corresponding to a given depth. The memory burden for the cross-sectional output is thus overwhelmingly smaller than that in the FFT scheme. Therefore, the employment of the lock-in particularly as a configuration for acquiring a high-definition two-dimensional cross-sectional pixel by an area sensor can allow the configuration to be mounted in the image sensor 100.

From the above discussion, the interference period should be shorter and the sampling frequency should be higher at the depth Z2 since the depth Z2 has a larger value (i.e., is deeper) than the depth Z1. In this case, the number of sampling at the time of extracting a signal component from the depth Z2 in one wave number sweep is made larger than the number of sampling at the time of extracting a signal component from the depth Z1. As a result, the number N of sampling can be increased within the same sampling time so that the S/N ratio of the signal, which is proportional to the square root of N, can be increased. This is effective particularly in preventing signal degradation due to noise, since the intensity of reflected light attenuates as the depth of the measurement plane in the subject 6 increases.

For the same reason, if more than two depths of the subject 6 are of interest, the number of sampling at the time of extracting the signal component from a depth in one wave number sweep can be made to increase as the depth of the subject 6 increases.

A pixel signal may first be sampled at the sampling frequency and then the obtained voltage signal may be locked-in by the reference signal having the interference frequency and be subjected to frequency separation. This can achieve an efficient configuration for desired measurement conditions as appropriate. In this case, for example, the current-voltage conversion circuit 300 illustrated in FIG. 2 has well-known selection circuit and multiplication circuit arranged upstream with respect to a position where the vertical signal line 310 inputs signals to the low-pass filter 400. Then, the transfer gate 303 transfers electric charges at a predetermined timing (e.g., in the shortest interval in which the on state and the off state can be switched) that is higher than the sampling frequency. The voltage signal obtained by the selection circuit sampling at the above-described sampling frequency is then locked-in and subjected to frequency separation by the multiplication circuit. The multiplication circuit then outputs the signal to the low-pass filter 400. In this case, the multiplication circuit serves as a multiplication unit.

The control processor 41 appropriately adjusts an image displayed on the display unit 50 and controls the entire measuring device 1. The control processor 41 constructs a three-dimensional image of the subject 6 based on obtained images at a plurality of depths of the subject 6. The control processor 41 applies processing for enhancing visibility on the constructed three-dimensional image, such as processing for enabling the user to observe the constructed three-dimensional image from a desired point of view, and outputs the three-dimensional image together with a two-dimensional image at a predetermined depth, as appropriate, to the display unit 50.

The control processor 41 adjusts the timing of the wavelength sweep by the oscillator 10 and the timing of the sampling by the image sensor 100 as needed. In the one-phase lock-in described above, the obtained signal intensity varies depending on a phase of the signal component at the time of the sampling. The amplitude can thus be detected with a high accuracy by adjustment of the phase.

The display unit 50 comprises a display device such as a liquid crystal monitor to display an image at a predetermined depth of the subject 6 or a three-dimensional image of the subject 6, which are constructed by the control processor 41.

Description of Stacked Image Sensor

The stacked image sensor 100 constituting the photoelectric converter 30 and the image processor 40 of the measuring device 1 will be described. The stacked image sensor 100 is described in WO13/164915 previously filed by the applicant and already published.

Figure 5:
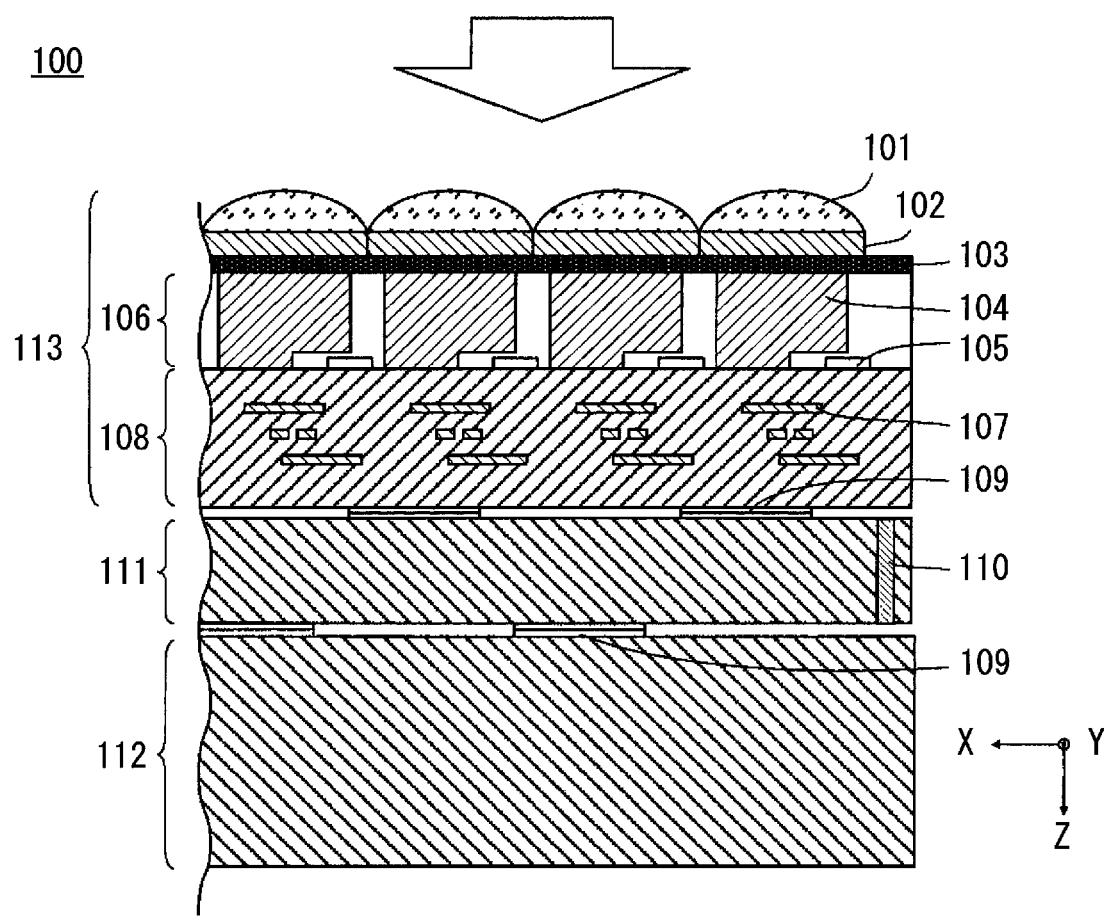
FIG. 5 is a cross-sectional view of a stacked image sensor according to one embodiment.

FIG. 5 is a cross-sectional view of the stacked image sensor 100. The image sensor 100 comprises a backside illumination image-capturing chip 113 that outputs a pixel signal corresponding to incident light, a signal processing chip 111 that processes the pixel signal, and a memory chip 112 that stores the pixel signal. The image-capturing chip 113, the signal processing chip 111, and the memory chip 112 are stacked and are electrically connected to each other by conductive bumps 109 made of Cu, for example.

It should be noted that incident light is incident mainly in a direction indicated by a white arrow as illustrated in the drawing. In the present embodiment, a surface of the image-capturing chip 113 on the side on which the incident light is incident is referred to as a backside surface (an image-capturing surface).

An example of the image-capturing chip 113 is a backside illumination CMOS image sensor. The image-capturing chip 113 physically embodies a part or all of functions of the photoelectric converter 30 in the functional blocks in FIG. 1. The PD layer 106 is disposed on the backside surface side of a wiring layer 108. The PD layer 106 comprises a plurality of PDs 104 that are two-dimensionally arranged and accumulate electric charges corresponding to incident light, and transistors 105 provided for the individual PDs 104.

On the light incident side in the PD layer 106, a filter layer 102 is provided via a passivation film 103. In the filter layer 102, a filter such as a polarizing filter is arranged as needed. A set of the filter layer 102, the PD 104, and the transistor 105 forms one pixel.

On the side of the filter layer 102 on which incident light is incident, a microlens 101 is provided for each pixel. The microlens 101 converges incident light toward the corresponding PD 104.

The wiring layer 108 has a wiring line 107 that transmits the pixel signal from the PD layer 106 to the signal processing chip 111. The wiring line 107 may be multilayered and may also be provided with passive elements and active elements.

A plurality of bumps 109 are disposed on a surface of the wiring layer 108. The plurality of bumps 109 are aligned with a plurality of bumps 109 provided on an opposing surface of the signal processing chip 111. The aligned bumps 109 are then joined and electrically connected to each other by a pressure applied on the image-capturing chip 113 and the signal processing chip 111 or by other measures.

Similarly, a plurality of bumps 109 are disposed on opposing surfaces of the signal processing chip 111 and the memory chip 112. These bumps 109 are aligned with each other. The aligned bumps 109 are then joined and electrically connected to each other by a pressure applied on the signal processing chip 111 and the memory chip 112 or by other measures.

It should be noted that the bonding of the bumps 109 is not limited to Cu bump bonding by solid phase diffusion and microbump bonding by solder melting may be employed. Additionally, only approximately one bump 109 is required for each of blocks which will be described later, for example. The size of the bump 109 may be thus larger than the pitch of the PD 104. In peripheral regions other than the pixel region where the pixels are arranged, bumps that are larger than the bumps 109 corresponding to the pixel region may also be provided together.

The signal processing chip 111 has a TSV (silicon penetrating electrode) 110 that connects a circuit provided on the front side surface to a circuit provided on the backside surface of the signal processing chip 111. The TSV 110 is preferably provided in the peripheral region. The TSV 110 may also be provided in the peripheral region of the image-capturing chip 113 or in the memory chip 112. The signal processor chip 111 is physically configured as an entity that embodies a part or all of functions of the image processor 40 in the functional blocks in FIG. 1. It should be noted that a part of the image processor 40 may be provided in the image-capturing chip 113.

The image sensor 100 described above has a processing circuit for a signal output for each pixel of the image sensor 100, and is physically configured as an entity that embodies a part or all of functions of the control processor 41 in the functional blocks in FIG. 1.

Figure 6:
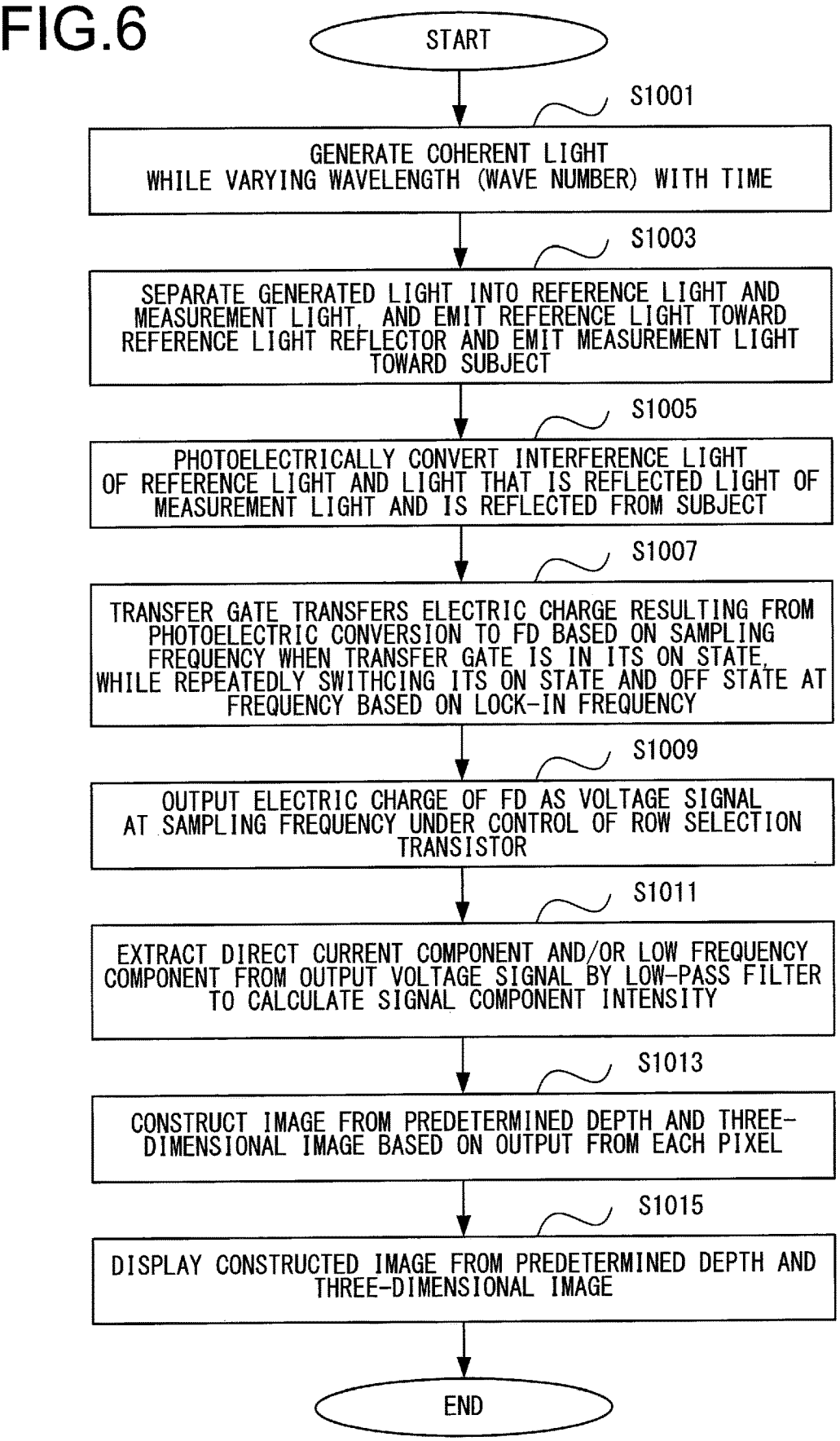
FIG. 6 is a flowchart illustrating a flow of creating an image from a predetermined depth of a subject.

FIG. 6 is a flowchart illustrating a flow of capturing and displaying an image at a predetermined depth of the subject 6 by the measuring device 1. The method illustrated in this flowchart allows a higher-definition OCT image to be obtained by frequency separation with a high accuracy using the lock-in.

In step S1001, the oscillator 10 generates coherent light while varying a wave number of the light with time. When coherent light is generated, the process proceeds to step S1003. In step S1003, the separator 20 separates the generated coherent light into reference light and measurement light, and then irradiates the reference light reflector 21 with the reference light and irradiates the subject 6 with the measurement light. After the irradiation with each light wave, the process proceeds to step S1005.

In step S1005, the photoelectric converter 30 photoelectrically converts the interference light of the reference light and the light that is reflected light of the measurement light and is reflected from the subject 6. When the interference light is photoelectrically converted, the process proceeds to step S1007. In step S1007, the transfer gate 303 repeatedly switches its on state and off state at a frequency based on a lock-in frequency, and transfers the electric charge resulting from the photoelectric conversion to the FD 305 based on the sampling frequency when the transfer gate 303 is in its on state. When the electric charge is transferred to the FD 305, the process proceeds to step S1009.

In step S1009, the image processor 40 outputs the electric charge of the FD 305 as a voltage signal at the sampling frequency under the control of the row selection transistor 309. When the voltage signal is output, the process proceeds to step S1011. In step S1011, the image processor 40 extracts a direct current component and/or a low frequency component from the output voltage signal by a low-pass filter. The image processor 40 calculates intensity of the signal component based on values of the obtained direct current component and/or low frequency component to output the intensity to the control processor 41. When the intensity of the signal component is output, the process proceeds to step S1013.

In step S1013, the control processor 41 constructs an image from a predetermined depth and a three-dimensional image based on the output from each pixel. The constructed image is output to the display unit 50. When the image is output, the process proceeds to step S1015. In step S1015, the display unit 50 displays the constructed image from the predetermined depth and three-dimensional image. When these images are displayed, the process is terminated.

According to the above embodiment, the following operational advantages can be achieved.

(1) The image sensor 100 according to the present embodiment comprises the image processor 40 that locks in and detects a signal component having an interference frequency in an interference light component corresponding to a predetermined depth from a signal output from the photoelectric converter 30. This prevents leakage errors, which would occur when frequency separation is performed by FFT or other schemes, and performs a high-Q filtering by a narrow-band low-pass filter based on the principle of lock-in amplifiers. The accuracy of the frequency separation can thus be improved.

(2) In the image sensor 100 according to the present embodiment, the image processor 40 is arranged for each pixel or for each block comprising two or more pixels, and locks in and detects the signal component having the interference frequency from a signal output from the photoelectric converter 30 of the corresponding pixel or block. This makes it possible to construct an image of the inside of the subject 6 at a high speed by parallel processing in the image sensor 100 and prolong the irradiation time by shortening the processing time, so that the intensity of the measurement light can be reduced accordingly. In this way, an effect of reducing the burden on subjects during, for example, fundus examination, observation of deep parts of living tissues by the endoscope or the like may be expected.

(3) The image sensor 100 according to the present embodiment has the processing circuit for a signal for each pixel or each block, and the processing circuit and the image processor 40 are arranged in a layer different from a layer where the photoelectric converter 10 is arranged. This can increase a light-receiving area on the image-capturing surface of the photoelectric converter 10 so that a higher definition image can be captured.

(4) In the image sensor 100 according to the present embodiment, the transfer gate 303 transfers a signal to the FD 305 when the transfer gate is in its on state while switching between its on state and off state at a frequency twice as high as the interference frequency. The image processor 40 comprises a low-pass filter 400 for separating a component having a low frequency equal to or less than a predetermined value and a direct current component from the signal output from the amplification transistor 308. An efficient lock-in can thus be achieved by using the transfer gate 303.

(5) The measuring device 1 according to the present embodiment comprises the image sensor 100. This can achieve an OCT with a high accuracy of frequency separation and with a high depth resolution in the subject 6.

The following variations are also encompassed within the scope of the present invention and may be combined with the above embodiment.

First Variation

In the above embodiment, polarization characteristics of the measurement light may be switched to temporally switch between a case where only the reference light is measured and a case where the interference light of the reference light and the light that is reflected light of the measurement light and is reflected from the subject 6 is measured. At this time, the filter layer 102 of the photoelectric converter 10 is provided with a polarizing filter.

Figure 7:
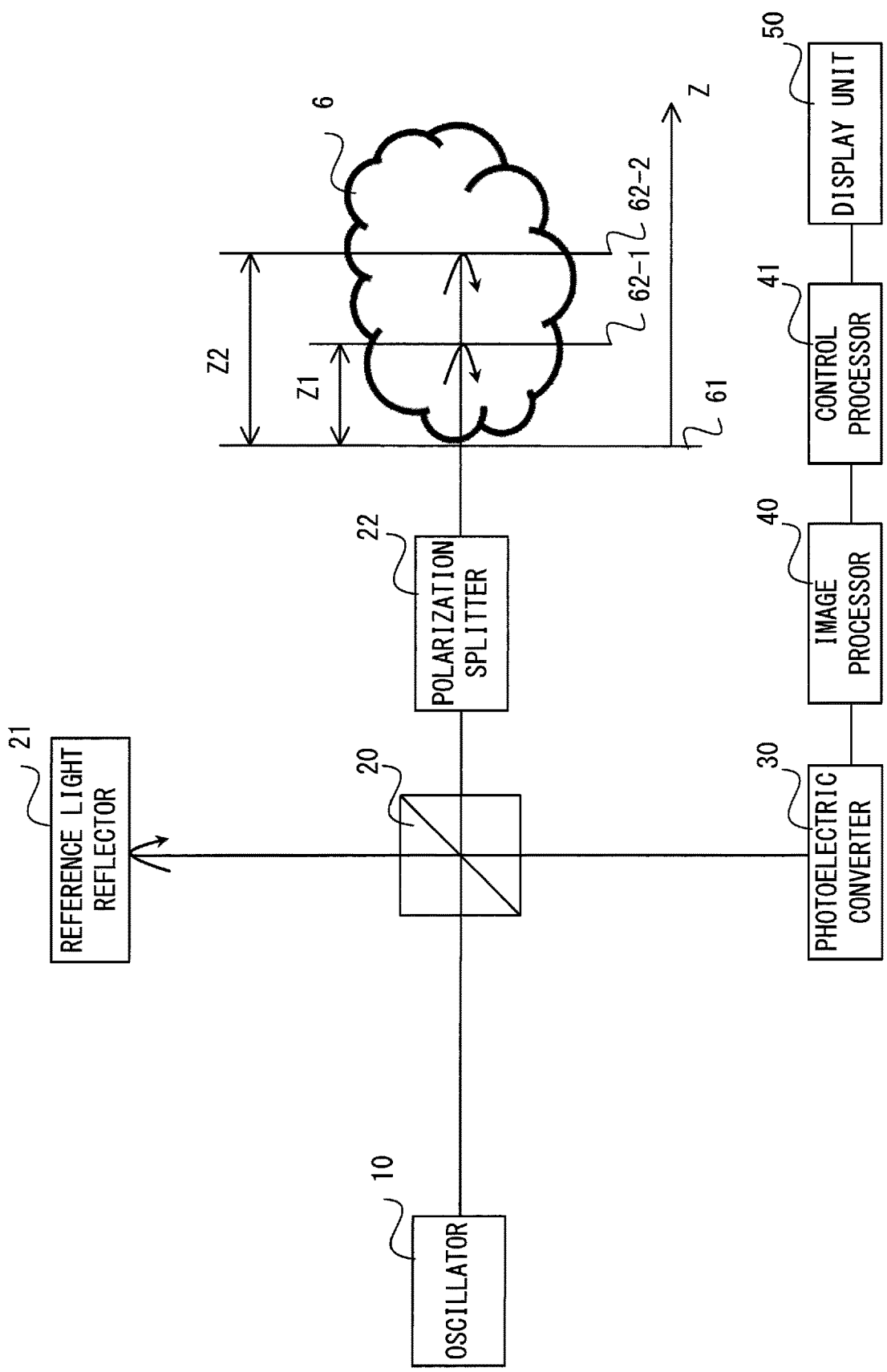
FIG. 7 is a schematic diagram of a measuring device in one embodiment.

FIG. 7 is a block diagram of a measuring device 1 configured to switch measurement light separated by the separator 20 between two polarization components orthogonal to each other in a polarization splitter 22. The polarization splitter 22 comprises a rotatable polarizer to convert the polarization of the measurement light to emit the light having a polarization component in a predetermined direction. The polarization splitter 22 switches the emitted light having the polarization component between a first polarized light component and a second polarized light component which is orthogonal to the first polarized light component. The first polarization component is orthogonal to a polarization component extracted by the polarizing filter arranged in the photoelectric converter 30. If the polarization splitter 22 emits light having the first polarization component in this configuration, the light is blocked by the polarizing filter so that only the reference light is photoelectrically converted in the photoelectric converter 10. On the other hand, if the polarization splitter 22 emits light having the second polarization component, interference light of the reference light and the light that is reflected light of the measurement light and is reflected by the subject 6 is photoelectrically converted. The image processor 40 removes noises or in-phase components shared by the measurement system from a signal resulting from the photoelectric conversion of the reference light. In this way, the S/N ratio of the signal output from the image processor 40 can be increased to construct a higher-definition image.

It should be noted that "orthogonal to" as used herein may include, for example, circularly polarized light or the like as long as two light waves having polarization components lose coherence due to the difference between polarization components. In the above description, the polarizing filter is arranged on the pixel of the photoelectric converter 30. Instead, a polarizing filter may be arranged between the separator 20 and the photoelectric converter 30.

Second Variation

In the above embodiment, one transfer gate 303 is provided for one PD 302 and a signal component from one depth is subjected to frequency separation. However, a plurality of transfer gates 303 may be arranged for one PD 302 and signal components from a plurality of depths may be subjected to frequency separation. This allows light waves from a larger number of different depths to be analyzed from the photoelectric converter 10 comprising a given number of pixels.

It should be noted that a signal component corresponding to one depth may be subjected to frequency separation by a plurality of transfer gates 303. This can address a high sampling frequency.

Figure 8:
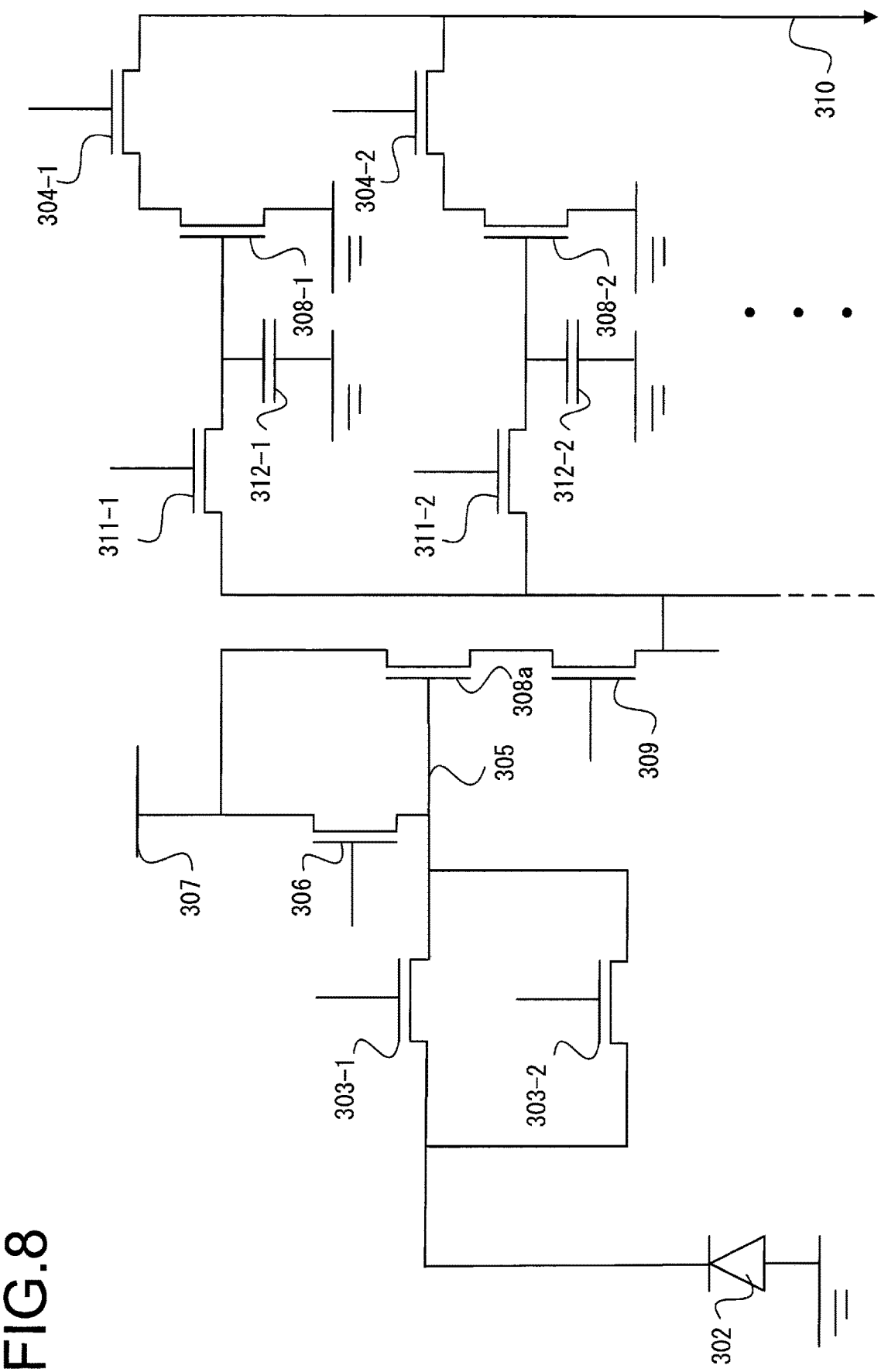
FIG. 8 is a schematic diagram illustrating a configuration of a processing circuit in a stacked image sensor according to one embodiment.

FIG. 8 is a diagram illustrating a circuit in which two transfer gates 303-1, 303-2 are arranged for one PD 302. In addition to the configuration of the circuit in FIG. 2, FIG. 8 also illustrates a sample hold circuit comprising a sample hold transistor (hereinafter referred to as an SH transistor) 311-1, a capacitor 312-1, a selection transistor 304-1, and an amplification transistor 308-1, and a sample hold circuit comprising a SH transistor 311-2, a capacitor 312-2, a selection transistor 304-2, and an amplification transistor 308-2. Although not illustrated in FIG. 8, a plurality of sample hold circuits are arranged in parallel to one another, in addition to the two sample hold circuits illustrated in FIG. 8. The two transfer gates 303-1, 303-2 are switched between an on state and an off state at different periods, and transfer electric charges resulting from the photoelectric conversion to the FD 305 at different sampling frequencies.

It should be noted that a reset system comprising a reset transistor and other elements is not illustrated in the sample hold circuit of FIG. 8.

A voltage signal from the amplification transistor 308a is controlled by the row selection transistor 309 and the SH transistors 311-1, 311-2 and is temporarily accumulated in the capacitors 312-1, 312-2 and the like of the sample hold circuit. The electric charges accumulated in the plurality of capacitors of the sample hold circuit are controlled and output so that different signals transferred from the transfer gates 303-1, 303-2 at different times are distinguished by the selection transistors 304-1, 304-2 and on the like.

In the circuit of FIG. 8, a PD may be provided for each of the transfer gates 303-1 and 303-2 so that current signals resulting from the photoelectric conversion in two pixels are converted into voltage signals by one amplification transistor 308a to appropriately store the information in a plurality of capacitors as electric charges, which are read out later. Similarly, one amplification transistor 308a may be used for a block comprising three or more pixels. Additionally, the lock-in may be performed at interference frequencies corresponding to different depths for each pixel. In this way, efficient processing for each block can be performed.

Third Variation

Although the transfer gates 303-1 and 303-2 are sampled at the same sampling frequency in the second variation described above, the switching between the on state and the off state in the transfer gates 303-1 and 303-2 may be shifted in phase by 180 degrees. In other words, the transfer gate 303-2 can be in the off state when the transfer gate 303-1 is in its on state and the transfer gate 303-2 can be in its on state when the transfer gate 303-1 is in the off state. The image processor 40 can calculate intensity of the signal component after the frequency separation by calculating, for example, the square-sum of the intensities of the signal components from the two transfer gates 303-1, 303-2. In this way, the configuration is equivalent to two-phase lock-in. This eliminates the need for phase adjustment, so that the intensity of a signal component corresponding to light from a predetermined depth can be more accurately calculated.

Fourth Variation

Although the reference light is reflected to interfere with the measurement light in the above embodiment, the reference light reflector 21 may be omitted.

Figure 9:
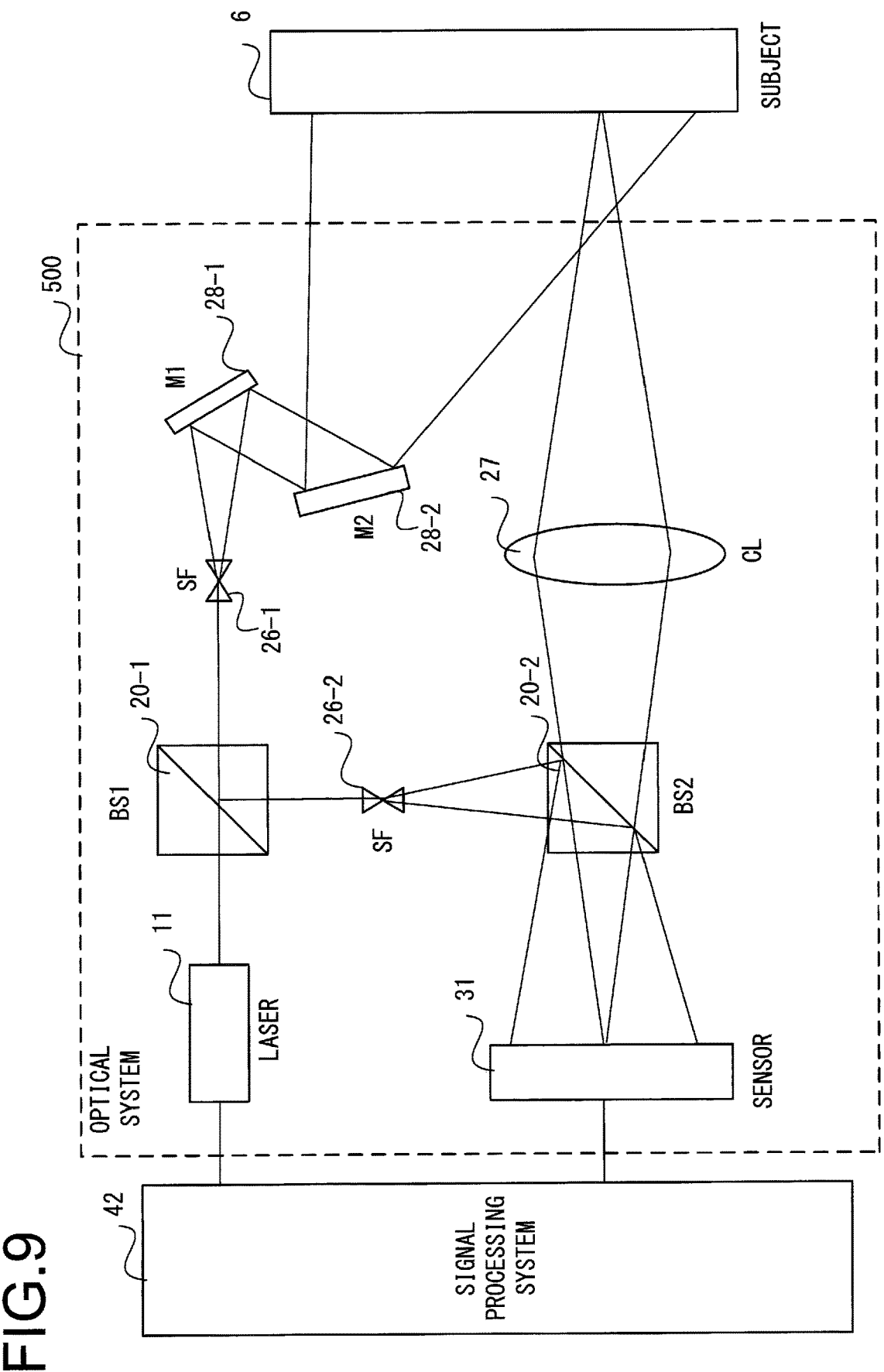
FIG. 9 is a schematic diagram of an optical system of a measurement device according to one embodiment.

FIG. 9 is a view illustrating an optical system 500 of a measuring device 1 without the reference light reflector 21. The optical system 500 comprises a laser 11, beam splitters 20-1, 20-2, SFs 26-1, 26-2, mirrors 28-1, 28-2, a collimating lens 27, and a sensor 31. The signal processing system 42 comprises a processor and other components. The signal processing system 42 controls the laser 11 and the sensor 31 and also performs analysis of image information from the sensor 31 and other processes. In FIG. 9, BS is an abbreviation of beam splitter, M is an abbreviation of mirror, and CL is an abbreviation of collimating lens.

A laser beam oscillated from the laser 11 is split into reference light and measurement light in the beam splitter 20-1. The measurement light emitted from the beam splitter 20-1 is diverged by the SF 26-1 to form diverging light and reflected by the mirrors 28-1 and 28-2. A surface of the subject 6 is then planarly irradiated with the measurement light. Light reflected from the subject 6 is incident on the beam splitter 20-2 through the collimating lens 27. The reference light emitted from the beam splitter 20-1 is diverged by the SF 26-2 to form diverging light and is then incident on the beam splitter 20-2. The reference light and the light that is reflected light of the measurement light and is reflected from the subject 6, which are incident on the beam splitter 20-2, are combined into interference light with which the sensor 31 as an area sensor is planarly irradiated. Such a configuration of the optical system without the reference light reflector 21 can reduce some noises.

Although not illustrated in the figure, a collimating lens may be combined with mirrors 28-1, 28-2 in the optical system for the measurement light. Furthermore, a collimating lens may be incorporated in an optical system between the reference light and the BS2 and an optical system from the BS2 to the sensor.

The present invention is not limited to the above embodiment. Other aspects contemplated within the technical idea of the present invention are also included within the scope of the present invention.

What is claimed is:

1. An image sensor that captures an image of light from a predetermined depth of a subject, comprising:
    a photoelectric converter that photoelectrically converts light comprising interference light of light from the subject and reference light, the interference light including interference light components of different frequencies each corresponding to a different depth of the subject; and a discrimination unit that performs frequency separation by locking-in and detecting a signal component having an interference frequency in an interference light component among the interference light components corresponding to the predetermined depth from a signal output from the photoelectric converter, the discrimination unit including:

a floating diffusion, and a transfer gate that transfers an electric charge resulting from the photoelectric conversion by the photoelectric converter to the floating diffusion when the transfer gate is in an on state while switching between the on state and an off state, the discrimination unit performing the locking-in by the transfer of the electric charge by the transfer gate.

2. The image sensor according to claim 1, wherein:
the image sensor comprises a plurality of pixels;
the photoelectric converter is arranged in each of the plurality of pixels; and
the discrimination unit is arranged for each pixel or for each block comprising two or more pixels, and locks in and detects a signal component having the interference frequency from the signal output from the photoelectric converter of the corresponding pixel or block.

3. The image sensor according to claim 1, wherein:
the discrimination unit is partly or entirely arranged in a layer different from a layer in which the photoelectric converter is arranged.

4. The image sensor according to claim 2, wherein:
the discrimination unit is partly or entirely arranged in a layer different from a layer in which the photoelectric converter is arranged.

5. The image sensor according to claim 1, wherein:
the electric charge transferred to the floating diffusion is output as a signal at a sampling frequency determined based on the interference frequency.

6. The image sensor according to claim 5, wherein:
the transfer gate transfers the electric charge to the floating diffusion when the transfer gate is in the on state while switching between the on state and the off state at a switching frequency based on the interference frequency; and
the discrimination unit further includes a filtering unit that separates a component having a low frequency equal to or less than a predetermined value and a direct current component from the output signal.

7. The image sensor according to claim 5, wherein:
the image sensor captures an image of interference light of light comprising light from a first depth and light from a second depth, the second depth being larger than the first depth, and the reference light, and
the sampling frequency corresponding to the second depth, is higher than the sampling frequency corresponding to the first depth.

8. The image sensor according to claim 2, wherein:
the image sensor captures an image of interference light of light waves from a plurality of depths and the reference light; and
the discrimination unit locks in and detects signal components having a plurality of the interference frequencies in a plurality of the interference light components corresponding to the plurality of depths from the signal output from the photoelectric converter, for each of the pixels or the blocks.

9. The image sensor according to claim 8, wherein:
the discrimination unit locks in and detects signal components having the plurality of interference frequencies in the plurality of interference light components corresponding to the plurality of depths from the signal output from the photoelectric converter, for each of the blocks; and
the interference frequencies for the plurality of pixels included in one of the blocks are different from each other.

10. A measuring device comprising:
the image sensor according to claim 1;
a wavelength variable light generator that generates wavelength variable light having a wavelength changed with time; and
a separator that separates the reference light and measurement light that is coherent with the reference light from the wavelength variable light generated by the wavelength variable light generator, and irradiates the subject with the measurement light.

11. The measuring device according to claim 10, wherein:
the wavelength variable light generator generates wavelength variable light having a wavelength varying with time in a near-infrared range.

12. The measuring device according to claim 10, further comprising:
a polarization splitter that splits the reference light into light having a first polarized light component and light having a second polarized light component, the second polarized light component being perpendicular to the first polarized light component, wherein:
the photoelectric converter comprises a first photoelectric converter that photoelectrically converts reference light of the first polarization component, and a second photoelectric converter that photoelectrically converts light comprising interference light of the reference light having the second polarization component and reflected light from the predetermined depth of the subject irradiated with the measurement light; and
the discrimination unit further includes a noise reduction unit that reduces noises of a signal output from the second photoelectric converter based on a signal output from the first photoelectric converter, wherein a signal component having the interference frequency is locked-in and detected from the signal output from the second photoelectric converter.

13. The image sensor according to claim 1, wherein the transfer gate transfers the electric charge to the floating diffusion when the transfer gate is in the on state while switching between the on state and the off state at a switching frequency twice as high as the interference frequency.

14. The image sensor according to claim 1, wherein
the interference light is a combination of light reflected from the subject and of reference light which is reflected from a reference light reflector, and
an area sensor of the photoelectric converter is planarly irradiated with the interference light.

15. A measuring method of measuring light from a predetermined depth of a subject by a measurement system comprising a light generator that generates coherent light, a separator that separates the light, a photoelectric converter, and a processor comprising a floating diffusion and a transfer gate that transfers an electric charge to the floating diffusion, the method comprising:
generating wavelength variable light having a wavelength changed with time, by the light generator;

separating reference light and measurement light that is coherent with the reference light from the wavelength variable light and irradiating the subject with the measurement light, by the separator;

photoelectrically converting light comprising interference light of the reference light and reflected light from the predetermined depth of the subject irradiated with the measurement light, by the photoelectric converter, the interference light including interference light components of different frequencies each corresponding to a different depth of the subject; and performing frequency separation by locking-in and detecting a signal component having an interference frequency in an interference light component among the interference light components corresponding to the predetermined depth from a signal output from the photoelectric converter, by the processor, wherein:

when the locking-in is performed, the transfer gate transfers the electric charge resulting from the photoelectric conversion by the photoelectric converter to the floating diffusion when the transfer gate is in an on state while switching between the on state and an off state, and the locking-in is performed by the transfer of the electric charge by the transfer gate.

* * * * *